United States Patent [19]

Wex et al.

[11] Patent Number: 5,633,140

[45] Date of Patent: May 27, 1997

[54] REACTION VESSEL FOR IMMUNOLOGICAL ANALYSIS OF AEROSOLS

[75] Inventors: Kerstin Wex, Lübeck; Thomas Wuske, Malente; Andreas Manns, Lübeck, all of Germany

[73] Assignee: Drägerwerk Aktiengesellschaft, Lübeck, Germany

[21] Appl. No.: 362,209

[22] Filed: Dec. 22, 1994

[30] Foreign Application Priority Data

Dec. 22, 1993 [DE] Germany ............... 43 43 842.3

[51] Int. Cl.$^6$ ........................... G01N 33/53
[52] U.S. Cl. ............ 435/7.1; 435/7.9; 435/7.93; 435/961; 435/963; 435/970; 436/518; 436/528; 436/530; 436/32; 436/178; 436/181; 436/810; 422/58; 422/83
[58] Field of Search ............... 435/7.1, 7.9, 7.92–7.93, 435/9, 961, 963, 970; 436/518, 528, 530, 533, 32, 140, 178, 181, 810; 422/58, 59, 60, 80, 82.05, 83, 86, 88

[56] References Cited

U.S. PATENT DOCUMENTS

| | | | |
|---|---|---|---|
| 4,300,910 | 11/1981 | Pannwitz | 422/102 |
| 4,458,020 | 7/1984 | Bohn et al. | 435/296 |
| 4,753,775 | 6/1988 | Ebersole et al. | 422/81 |
| 4,943,522 | 7/1990 | Eisinger et al. | 435/7.92 |
| 4,977,095 | 12/1990 | Zaromb | 436/178 |
| 5,116,759 | 5/1992 | Klainer et al. | 435/288 |
| 5,183,740 | 2/1993 | Ligler et al. | 435/7.32 |

FOREIGN PATENT DOCUMENTS

| | | |
|---|---|---|
| 3448006 | 12/1987 | Germany . |
| 3914801 | 11/1990 | Germany . |
| 4126436 | 3/1992 | Germany . |

OTHER PUBLICATIONS

"A continuous flow immunoassay for rapid and sensitive detection of small molecules" by A. Kusterbeck et al, Journal of Immunological Methods, vol. 135, (1990), pp. 191 to 197.

"Dräger-Röhrchen Handbuch", published by Drägerwerk Aktiengesellschaft Lübeck, 1991. No Translation.

"The Measurement of Antibody Affinity: a Comparison of Five Techniques Utilizing a Panel of Monoclonal Anti-DNP Antibodies and the Effect of High Affinity Antibody on the Measurement of Low Affinity Antibody" by C. Stanley et al, Journal of Immunological Methods, vol. 54, (1983), pp. 119 to 132.

*Primary Examiner*—Carol A. Spiegel
*Attorney, Agent, or Firm*—Walter Ottesen

[57] ABSTRACT

A unitary collection and displacement immunoassay device for determining a toxic substance adhered to aerosols in the air is provided. The device comprises an elongated body having proximal and distal ends and encloses a space defining a collection chamber, a reaction chamber and a measurement chamber, each chamber separated by a liquid flow barrier which delays liquid transport between chambers until a vacuum source is applied to the distal end of the test device to pull liquid into the next chamber. The collection chamber contains a solution for solubilizing the toxic substance from the aerosols and a semi-permeable means for separating the solubilized toxic substance from the aerosols. The reaction chamber contains a labelled immunoreactant bound to a solid phase carrier material. The labelled reagent can be displaced by the solubilized toxic substance. The measurement chamber contains a color generating system which reacts with displaced labelled reagent to produce a colored product in proportion to the concentration of the toxic substance.

20 Claims, 6 Drawing Sheets

REACTION VESSEL FOR IMMUNOLOGICAL ANALYSIS OF AEROSOLS

FIELD OF THE INVENTION

The invention relates to a reaction vessel for making a rapid qualitative and/or quantitative determination of so-called air toxic aerosols with the aid of an immunochemical reaction wherein specific antibodies are utilized for selectively binding the air toxic aerosols and a marking or system for displaying or identifying this bond is utilized.

BACKGROUND OF THE INVENTION

Dry air is chemically a gas mixture. Air contaminants by a multiplicity of substances change the composition of this gas sometimes considerably. In this context, chemical compounds have special significance either in solid form or sorptively bonded on or to coarse or fine dust particles. These dust particles are supplied to the normal air either by natural processes (for example, by vulcanizing action) or by the activity of people.

These so-called environmental chemicals can be roughly classified as gases and aerosols based on their physical characteristics. Of great significance are those environmental chemicals (that is, environmental noxae such as allergens, pesticides and the like) which occur to an increasing extent as a toxic substance burden of outside and indoor air of persons and animals. Burdening of the air by coarse and fine dust can be especially seen in large cities and industrial areas. Dust having particles below 5 micrometers obtain access to the lungs, that is, they enter the alveoli. These particles can collect there or pass into the blood, penetrate into body cells and damage their metabolic enzymes, trigger allergies and the like. If several environmental noxae appear simultaneously in the air, then synergistic effects are possible.

Aerosols are by definition two-phase systems in which solid or liquid particles/substances are finely dispersed in a gas phase; that is, in these two-phase systems, air functions as a carrier and distribution medium for these particles/substances. If, for example, biological materials such as spores, viruses or bacteria are dispersed in air, then this can be characterized as biological aerosols or bioaerosols; so-called solid aerosols are those which contain solid substances in dispersion. The size distribution of particles contained in aerosols extends over a spectrum of particles having diameters of $10^{-3}$ micrometers up to approximately $10^2$ micrometers. This large range can be explained from the multiplicity of possibilities of origin and different physico-chemical composition of air contaminating particles.

Particle size is directly associated with the parameters determining the biological effect, namely, dwell duration in the air, chemical activity and lung deposits. The deposits of particles in persons concerns a size range of from 0.03 to 20 micrometers particle diameter. The fine dust component (<10 micrometer) comprises in so-called house dust only about 20% of the total dust mass but can contain up to 90% of the substances which act toxically or as allergens. For this reason, aerosols (in this context, dangerous substances carried in air) define a health risk in interior spaces, living and working spaces, transportation means, hotels and the like, which should not be underestimated.

In order to exclude health dangers, for example at the workplace, specific limit values are defined in appropriate statutes. If the occurrence of dangerous substances (aerosols) cannot reliably be excluded in the air at the workplace, then the workplace has to be monitored with respect to a drop below the limit values (maximum workplace concentration, permitted concentration, biological workplace tolerance value). Such a monitoring can be performed by taking measurements.

At the present time, an extensive assortment of testing tubes is available for making quantitative rapid analysis of gases, vapors and aerosols in the range of maximum workplace concentration values. When making the measurement, the tips of the testing tube are broken off and the testing tube is introduced into an appropriate gas pump and the prescribed gas or air volume is drawn by this pump through the reaction layer. Most testing tubes are so-called scale tubes for which the indicating layer is colored over a length dependent upon the analyte concentration.

Furthermore, testing tubes having a color comparison layer are known with which a color comparison is made after the reaction. The basis for most testing tubes are pure chemical reactions of the gas or aerosol to be measured with the chemicals of the tube arranged in a layer or layers. In this context, reference can be made to the "Dräger-Röhrchen Handbuch", eighth edition (1991) published by Dr ägerwerk AG, Lübeck, Germany.

One-way reaction vessels or testing tubes are known wherein gaseous toxic substances are detected with the aid of an enzymatic reaction. In this connection, reference may be made to U.S. patent application Ser. No. 07/448,235, filed Dec. 11, 1989, and German patent publication 3,914,801.

It should be noted that there is a number of toxic substances which cannot be measured enzymatically or with conventional physical-chemical methods but only by means of complex enriching and analyzing methods. Immunochemical methods (immunoassays) as they are routinely utilized in the clinical analysis or food analysis for detecting various substances have, in recent times, also been utilized for determining environmental chemicals in earth and water samples and are described, for example, in a paper of Van Emon et al entitled "Immunochemical Methods for Environmental Analysis", ACS Symposium Series 442, (1990) ACS Washington, D.C.

Up to now, multipurpose reaction vessels or reusable columns which are packed with antibodies or antigens (analytes) bonded to a solid carrier have been used in immunoassays while utilizing the so-called affinity chromatography as an important method step.

German patent publication 4,126,436 discloses a one-way reaction vessel for making a solid-phase immunoanalysis. The one-way reaction vessel is in the form of a one-way column which makes possible carrying out an immunoassay and which is suitable for immediate use without previous calibration or regeneration measures. The one-way reaction vessel is open at the upper and lower ends and is for making a solid-phase immunoanalysis with two porous partitioning devices which are disposed therein and are permeable for liquids. At least one immunological reactive component is disposed between the partition devices and is applied to a carrier material. The through-flow speed of the liquids is then determined by the permeability of the upper and/or lower partitioning device. Furthermore, the high charging density of the carrier material with the active components causes the component to be determined to bond to the reactive components almost completely within approximately 1 minute before the through-flowing liquid exits from the carrier bed volume.

According to procedure, the component to be determined in the specimen is retained by the immunological reactive component in the one-way reaction vessel. The component is then, for example, determined via a marked compound competing with the component to be determined. Even when the one-way vessel and the detection method disclosed in German patent publication 4,126,436 is simplified when compared with earlier immunochromatographic methods, it cannot be utilized directly for detecting toxic aerosols carried in air. Furthermore, the immunochemical detection includes additional method steps between specimen application and detection such as: washing, elution and marking identification (fluorescence identification). The last step requires, in addition, a special peripheral apparatus.

SUMMARY OF THE INVENTION

It is an object of the invention to provide a simple, directly indicating reaction vessel, which can be directly evaluated for such environmental chemicals, preferably aerosols which cannot be enzymatically directly measured or measured with conventional physical-chemical methods but only with complex enrichment and analysis methods.

The reaction vessel of the invention is for determining a toxic substance adhering to aerosols in an air sample. The reaction vessel includes: a body enclosing a space and defining a through-flow direction; at least one breakable ampule disposed in the space and being filled with a reagent solution for dissolving and removing/separating the toxic substance from the aerosols and for transporting the toxic substance in the through-flow direction; a collecting layer arranged in the space downstream of the ampule for holding back the aerosols; an immunochemical reactive charge including a carrier material and an immunological reaction component bonded to the carrier material; a reaction chamber arranged in the space downstream of the collecting layer to receive the reagent solution and the toxic substance; the reaction chamber holding the immunochemical reactive charge which together with the toxic substance and the reagent solution are converted into a toxic substance solution in an immunochemical displacement process wherein the toxic substance operates as an analyte; a first flow-transport impeding layer disposed between the collecting layer and the reaction chamber; a color-imparting system for imparting a color to the toxic substance solution which is proportional to the concentration of the toxic substance in the air sample; measuring chamber means arranged in the space downstream of the reaction chamber for determining the concentration of the toxic substance in the air sample based on the color reaction; and, a second flow-transport impeding layer disposed between the reaction chamber and the measuring chamber means.

The reaction vessel according to the invention is referred to in the following also as a testing tube wherein all necessary reagents (antibodies, tracer, substrates, buffers, and the like) are a direct component of the testing tube. The air sample is drawn by suction directly into the testing tube by means of a gas pump and the aerosol is collected and enriched in this manner. Additional manipulation steps such as applying or metering the specimen and additional solutions with conventional laboratory devices or pipetting machines are not necessary. In this way, a direct measurement/monitoring is possible which, for example, can take place at the workplace or generally indoors.

The invention proceeds from proven testing tubes as they are described, for example, in the publication referred to above, namely, "Dräger-Röhrchen Handbuch", eighth edition (1991) and published by Drägerwerk AG of Lübeck, Germany. In this publication, testing tubes are known which contain one or even more breakable ampules with liquid reagents. The testing tube is breakable in the region of the ampule and is provided, for example, with a tube jacket. In the invention, the ampules are arranged individually or two are placed one next to the other or one behind the other. With this configuration, the possibility is provided to store liquid reagents in the testing tube without them coming into contact with the other "fillings" (coated carriers, lyophilized reagents, collecting layers and the like).

When the testing tube is utilized, it is broken at the breakable location at the time point correct for each reaction. The ampule then breaks and its contents pour over the interior of the tube. An especially advantageous feature is described in U.S. Pat. No. 4,300,910. For the evaluation of the chemical reaction, which has taken place, the degree of coloration of a liquid to be collected in a previously empty testing tube chamber (measuring chamber) is utilized. The liquid block comprises hydrophobized fabric (paper) and prevents the reagent liquid from exiting into the intake pump (gas pump) and therefore prevents damage to the pump.

In the present invention, this testing tube segment is applied for measurement evaluation in a manner similar to U.S. Pat. No. 4,300,910. The evaluation can then be carried out with the unaided eye by comparison to a color standard or can be carried out spectrophotometrically utilizing equipment. Furthermore, this tube region can be the reaction place because reagents can be stored within the tube region, for example, in lyophilized form. These reagents are rehydrated only after being brought into contact with liquid and are, for example, used as an enzyme substrate. Furthermore, or in the alternative, a further reagent ampule can be integrated into this region.

The testing tube according to the invention including the immunologic method can be suitably utilized as a simple and rapidly manipulable evaluation unit which can be evaluated directly qualitatively and/or quantitatively. This is because the combination of the detection method, which is on the basis of an immunological displacement test (displacement assay) in combination with testing tube technology. This testing tube technology today belongs to the classical measurement methods of the gas and air analysis. A rapid analysis of air samples is furthermore possible because the one-way reaction vessel permits immediate use since the reagents, solutions, carrier materials and the like contained therein are standardized and must not be calibrated in advance of being utilized. In this way, and for the first time, a direct measurement/monitoring of toxic aerosols carried in air is made possible, for example, at the workplace or generally indoors. This measurement/monitoring is rapid, reliable, and cost effective and the analysis is simple in its manipulation at the location and this was not previously available at the location of intended use.

The invention will be explained below in greater detail in the context of examples and with respect to the corresponding figures in the drawings. In the example of the immunochemical reaction and the participating reaction components, dinitrophenol-lysine (DNP-L) is used as an analyte and DNP-L conjugates are used as tracers. The monoclonal anti-dinitrophenol antibody is used as a specific antibody. This antibody is described in the paper of C. Stanley et al entitled "The measurement of antibody affinity: a comparison of five techniques utilizing a panel of monoclonal anti-DNP antibodies and the effect of high affinity antibody on the measurement of low affinity antibody" published in the Journal of Immunological Methods, 64 (1983), pages 119 to 132. In the examples, testing tubes will be discussed as the reaction vessel for the sake of simplicity even though other embodiments can be used.

BRIEF DESCRIPTION OF THE DRAWINGS

The invention will now be described with reference to the drawings wherein.

DESCRIPTION OF THE PREFERRED EMBODIMENTS OF THE INVENTION

FIGS. 1 to 8 show a testing tube 1 made of glass. The ends of the testing tube 1 are configured as respective breakable tips (2, 3). A first chamber 6 is arranged at a first location viewed in the through-flow direction 5. One or two breakable ampules (7, 28, 29, 32, 33) are accommodated in the first chamber 6. A shrunk-fit tube 8 is pulled over the glass tube 1 at the elevation of the ampules (7, 28, 29, 32, 33). A collecting layer 9 is located downstream of the first chamber 6. This collecting layer 9 comprises inert PTFE membranes of defined pore size (between 0.45 and 5 micrometers). This collecting layer 9 is followed by a supporting hydrophobized felt layer. In addition, a granular inert quartz layer having grains of 0.5 to 0.8 mm can also be provided (not shown). An immunochemical reactive charge 11 is arranged in the next reaction chamber 10 and is followed by a measuring chamber 12. The individual charges 11 or chambers (6, 10, 12) of the testing tube 1 are held against movement by holding elements (13, 14, 15, 16, 17, 26). In addition, the individual tube chambers (6, 10, 12) are closed off in flow direction 5 with the blocking layers (18, 19, 24) made of hydrophobized filter material. The blocking layers (18, 19, 24) retard the liquid transport. A liquid block 20 at the end 3 of the testing tube 1 prevents the exit of liquid.

In the testing tube in FIGS. 3 to 8, an enzyme reaction chamber 25 is provided between the holding element 16 and the measuring chamber 12. The enzyme reaction chamber 25 includes the holding element 26 and the blocking layer 24. The configuration of the components or reagents in the enzyme reaction chamber 25 and in the measuring chamber 12 can be stored in dry form (27, 38), as impregnated granular reaction layer 49 or in a breakable ampule (36, 39).

EXAMPLE 1

Aerosol Testing Tube Configuration

The immunochemical detection of toxic aerosols entrained in air is carried out with the testing tube (FIG. 1) according to the invention as described below.

Figure 1:
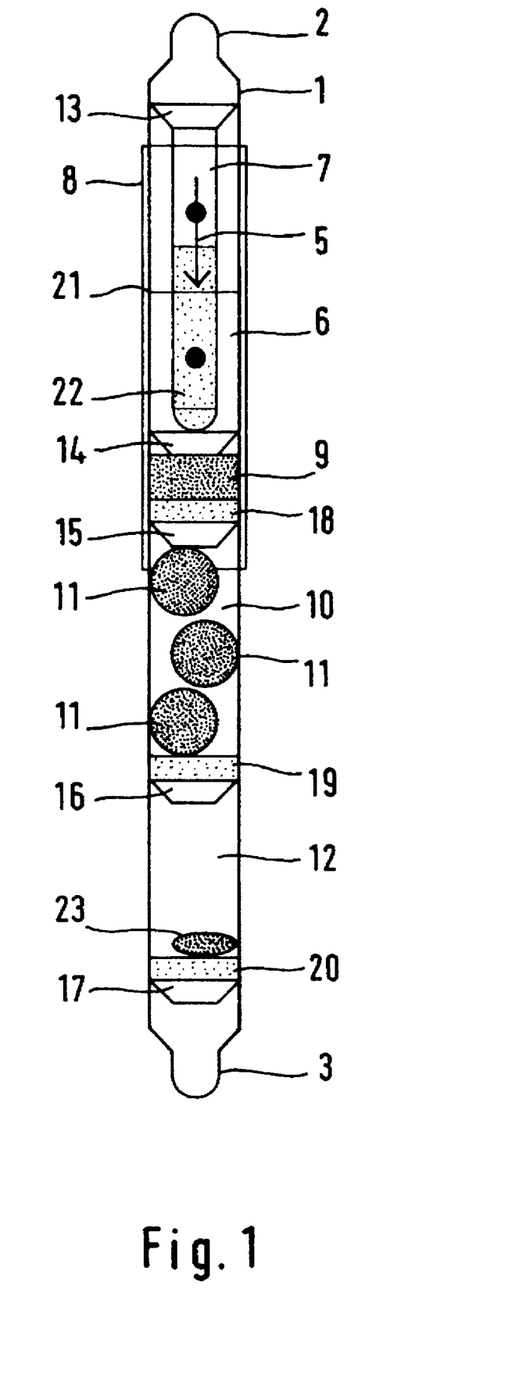
FIGS. 1 to 8 show various embodiments of testing tubes in longitudinal section for immunologically detecting aerosols.

The tips (2, 3) on the glass testing tube 1 are broken off and the testing tube is then placed in a gas pump. Thereafter, testing air, for example, 10 to 100 liters are drawn by suction through the tube in the through-flow direction 5. While taking this air sample, the aerosol present in the air sample is deposited and collected (accumulated) in the chamber 6, but preferably on the adjoining collection layer 9. Thereafter, the breakable ampule 7 is broken at the brake location 21. In this way, the ampule solution 22 enters the chamber 6 and reaches the collecting layer 9 by shaking. The nature of the solution 22 with which the ampule 7 is filled is dependent upon the particular aerosol to be investigated. The ampule solution 22 is so selected that, on the one hand, an excellent solubility of the toxic substances adhering to the aerosol particles is obtained, while, on the other hand, the immunochemical reaction which follows is not inhibited. Accordingly, it can be expected that bioaerosols, which contain so-called exines (allergenic proteins or peptides) as toxic components, will require different characteristics of the ampule solution 22 with respect to the solubility of the exines than will pesticides or other aerosol forming chemical compounds.

After breaking the ampule 7 and after the deposited aerosol and the ampule solution 22 are brought into contact, the testing tube 1 is allowed to stand at, for example, room temperature for several minutes (for example, 5 to 20) depending upon the solubility of the toxic material to be investigated. A direct transfer of the toxic solution so produced into the following reaction chamber 10 is prevented, that is, delayed, by a blocking layer 18. The testing tube 1 must be held perpendicularly for the complete transfer of the solution 22 from the chamber 6 and collection layer 9 into the reaction chamber 10 and the toxic solution must be pulled by suction with the gas pump into the reaction chamber 10. The immunoreaction (FIG. 10) takes place during the passthrough of the toxic substance solution through the reaction chamber 10 along the immunochemical reactive charge 11. A direct transfer of the toxic substance solution from the reaction chamber 10 into the measuring chamber 12 is prevented, that is, delayed, by a blocking layer 19.

After a defined reaction time (for example, 5 to 20 minutes) the toxic substance solution is again drawn by suction from the reaction chamber 10 into the measuring chamber 12 by means of the gas pump. This measuring chamber 12 is used for measurement evaluation, for example, by means of a visible coloration. For the immunoreaction according to the invention, the aerosol toxic substance concentration is directly proportional to the color-generating marking concentration so that the resulting color intensity in the measuring chamber is directly proportional to the quantity of toxic substance. The evaluation of the various marking intensities is possible with the unaided eye as well as with the aid of optoelectrical scanning equipment. In the case of color markings, the different color intensities are compared to a color standard.

Figure 2:
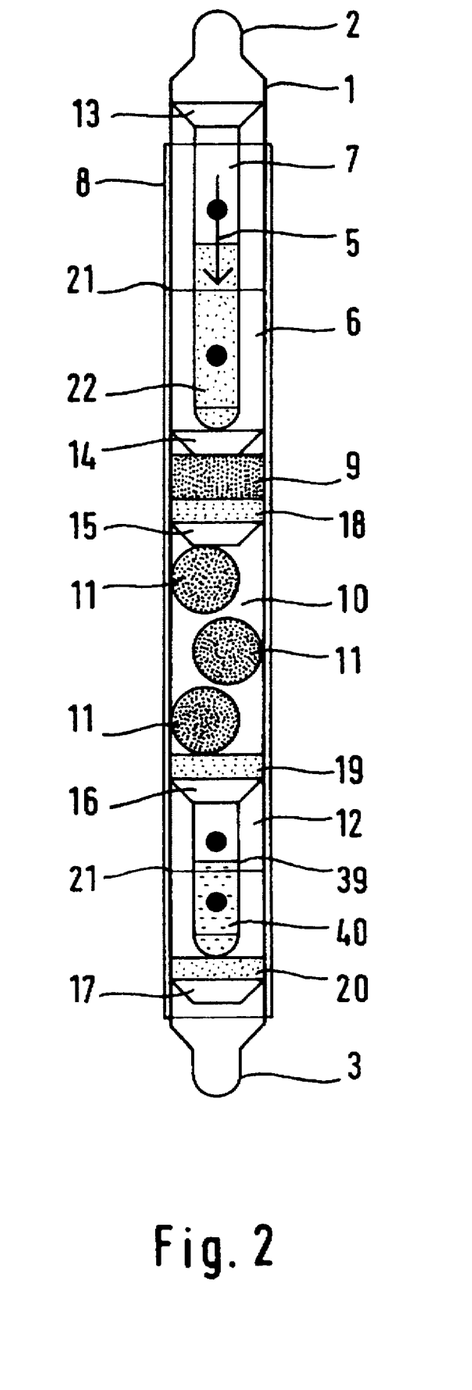

In the present invention, the measuring chamber 12 is simultaneously the chamber for the enzyme reaction in those cases wherein enzymes are used as color-imparting components. For example, reagents (substrates, salts or buffer substances) are stored in the measuring chamber 12 in dry lyophilized form 23 or as a solution 40 in a breakable ampule 36 (FIG. 2). Only at the desired time point, when the liquid from the reaction chamber 10 flows into the measuring chamber 12, are these reagents rehydrated (in the case of the lyophilisate 23) and converted as a colorless enzyme substrate by the immunochemically released enzyme tracers into a detectable coloration. The incubation and the following evaluation take place pursuant to a defined time schedule. The liquid block 20 is made of hydrophobized paper and prevents the reagent liquid from exiting into the intake pump and therefore prevents damage to the latter.

In a further embodiment (FIGS. 3 to 8), the reaction chamber 10 is provided with an additional blocking layer 24 and a holding element 26. In this embodiment, an enzyme reaction chamber 25 is arranged directly after the reaction chamber 10. The enzyme reaction chamber 25 contains specific color-imparting enzyme substrates for the enzyme tracers; that is, in FIG. 7, this is in dry form 38, in FIGS. 3 to 6, as a granular reaction layer impregnated with an enzyme substrate 23 and in FIG. 8 in a breakable ampule 39.

Figure 6:
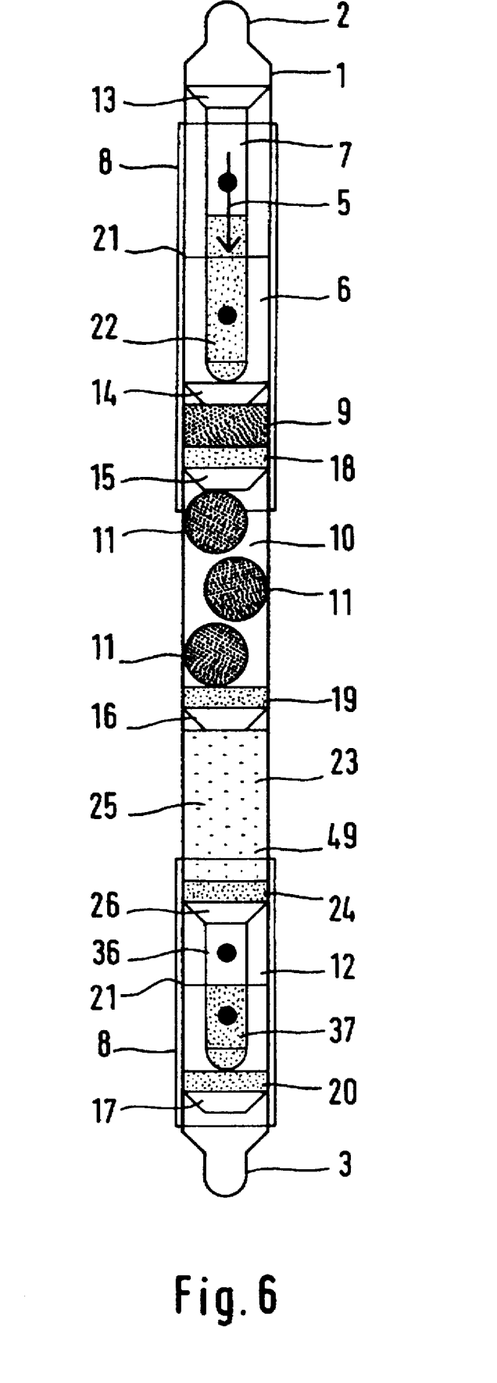

The immunoreaction according to the invention takes place in the reaction chamber 10. Thereafter, for example, after 5 to 20 minutes, the solution is drawn by suction from the reaction chamber 10 into the enzyme reaction chamber 25 by means of the gas pump. The enzymatic conversion takes place in the enzyme reaction chamber 25 and is, for example, a conversion of colorless substrates to color-imparting products. The more-or-less colored liquid is drawn by suction from the enzyme reaction chamber 25 into the measuring chamber 12 after a defined reaction time with the aid of the gas pump. According to the invention, in this embodiment, enzyme inhibiting reagents 27 are disposed in the measuring chamber 12 in lyophilized form and stop the coloring reaction after rehydration by means of the incoming liquid and, in this way, generate a measuring signal stabilized over a long time. In the embodiment of FIG. 6, the enzyme inhibiting reagents are present as a solution 37 in a breakable ampule 36.

Figure 3:
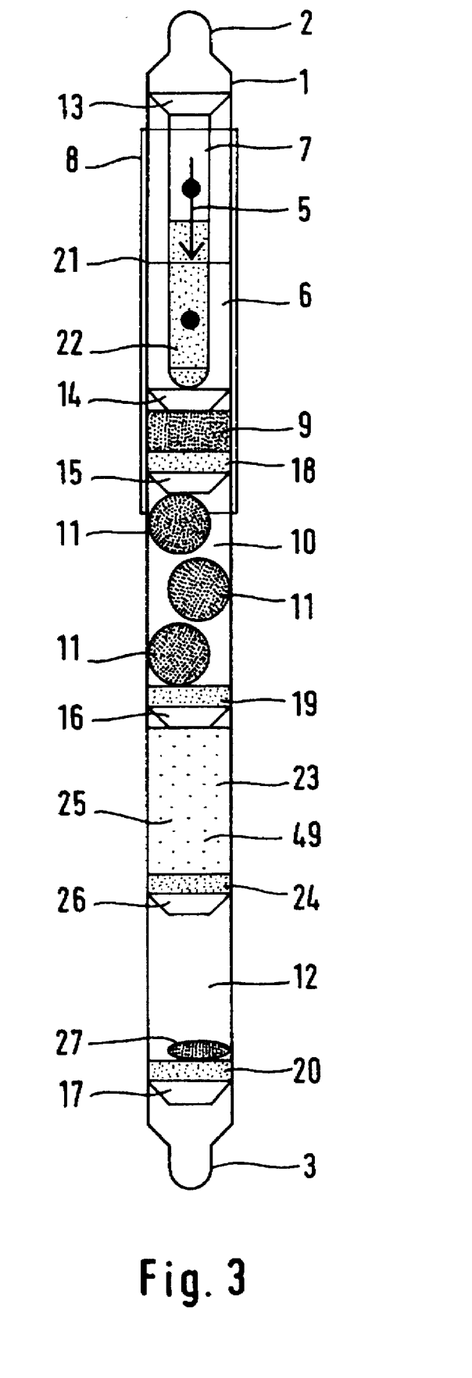
Figure 4:
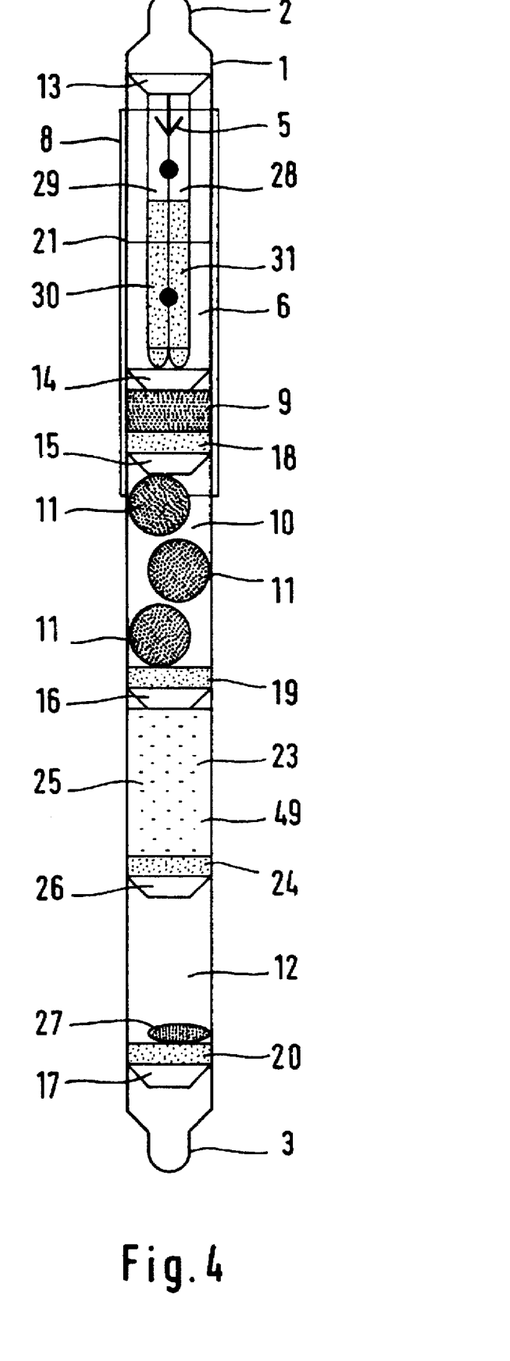

The embodiment of the invention shown in FIG. 4 has the same component composition as in FIG. 3. In the embodiment of FIG. 4, the ampule 7 is replaced, for example, by two breakable ampules 28 and 29 arranged side by side. The breakable ampules 28 and 29 contain ampule charges 30 and 31, respectively. This arrangement of the ampules makes possible storing ampule solutions for the follow-on aerosol reaction which, for example, in the mixed state are: chemically incompatible, unstable, cannot be stored and the like.

Figure 5:
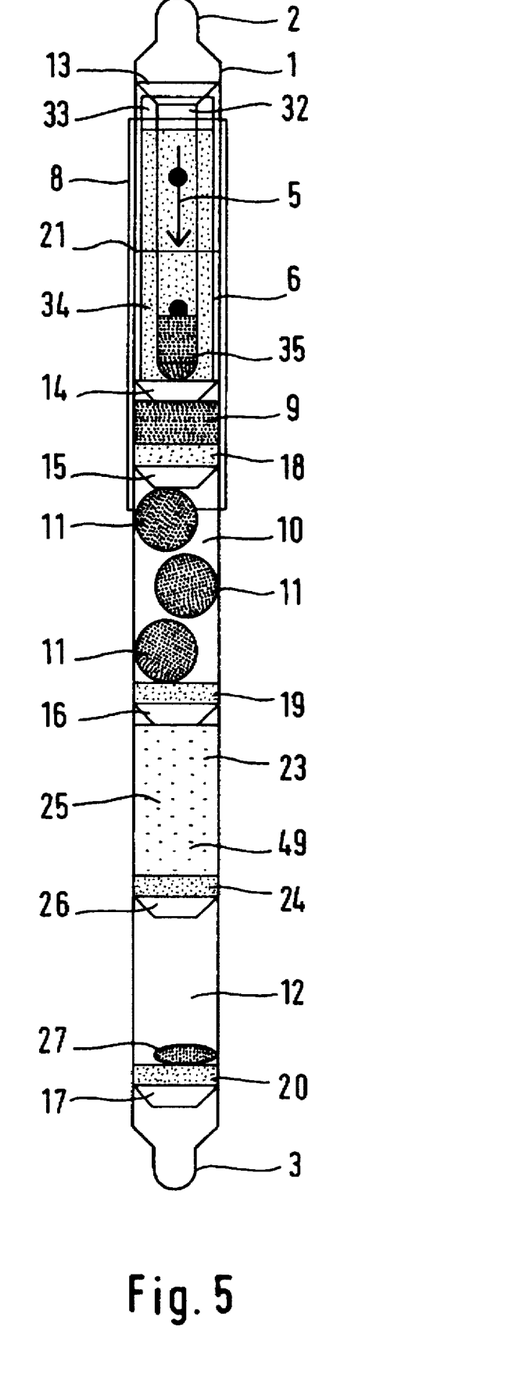

A further embodiment of the invention is shown in FIG. 5 and has the same constituent composition as that shown in FIG. 3. In the embodiment of FIG. 5, the ampule 7 is replaced by two breakable ampules 32 and 33 containing ampnle charges 34 and 35, respectively. These ampules 32 and 33 are arranged one inside the other. This embodiment permits the simultaneous storage of reagents in two different phases such as a reagent solution or a buffer in liquid form 34 and reagents as a dry substance 35. If the double ampule (32, 33) is broken at a pregiven time point at the break location 21, the dry reagent substance 35 is dissolved by the buffer 34 and can be utilized thereafter as a use-ready ampule reagent for detecting aerosols as described.

A further embodiment of the invention is shown in FIG. 6 and has the same constituent composition as that shown in FIGS. 1 or 3. In the embodiment of FIG. 6, the reagent 23 and reagent 27, which are stored as dry substances in the measuring chamber 12, are replaced by a breakable ampule 36 having the ampule solution 37. This arrangement makes possible the storage of liquid reagents in the region of the measuring chamber 12.

Figure 7:
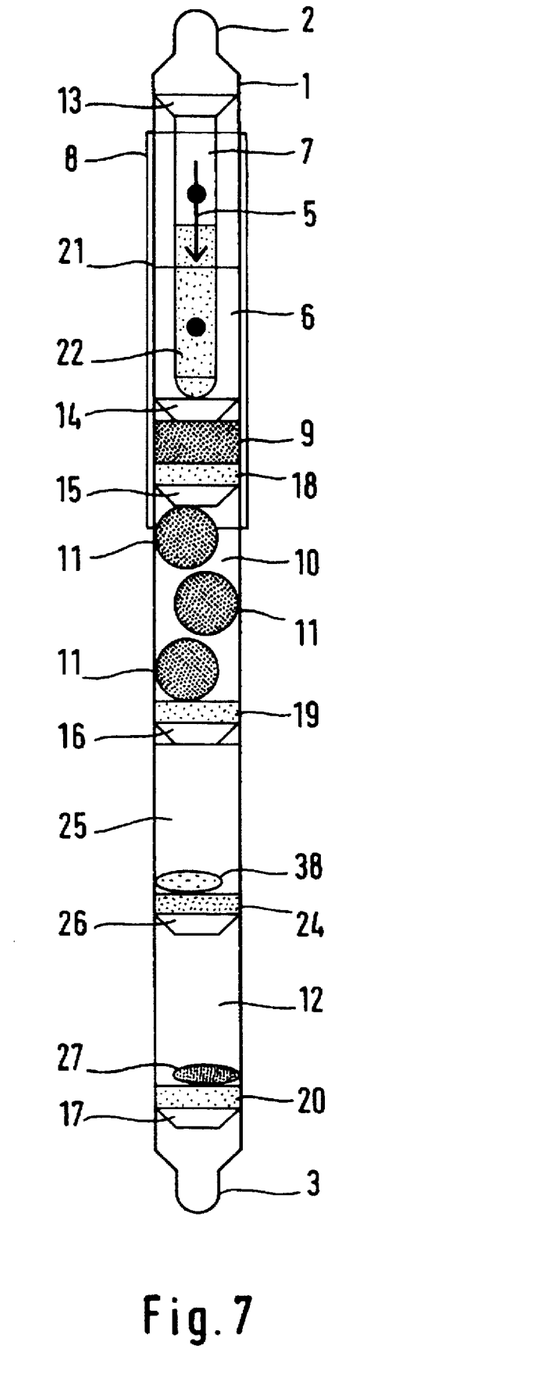
Figure 8:
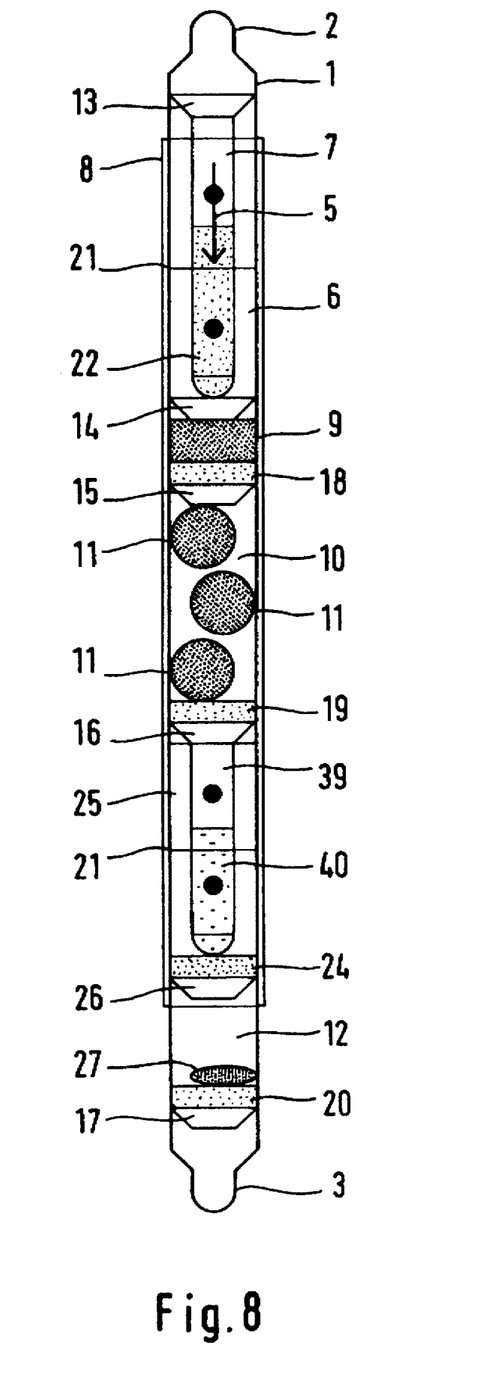

The embodiments shown in FIGS. 7 and 8 have a constituent composition analog to the embodiment shown in FIG. 3. In the embodiment of FIGS. 7 and 8, the charge of the enzyme reaction chamber 25 is varied. If the enzyme reaction chamber 25 in FIG. 3 contains a dry, granular carrier 49 impregnated with specific color-imparting substrates 23, then, in FIG. 7, the specific color-imparting enzyme substrates are stored as a pure reagent lyophilisate such as in powder or pill form 38 and, in FIG. 8, as ampule liquid 40 in an additional breakable ampule 39. The determination which of the above exemplary embodiments is applied is decisively influenced by: the physicochemical characteristics of the aerosol to be detected and the additional reaction constituents, the quality of the antibodies and the stability and storability of the reagents used.

Figure 9:
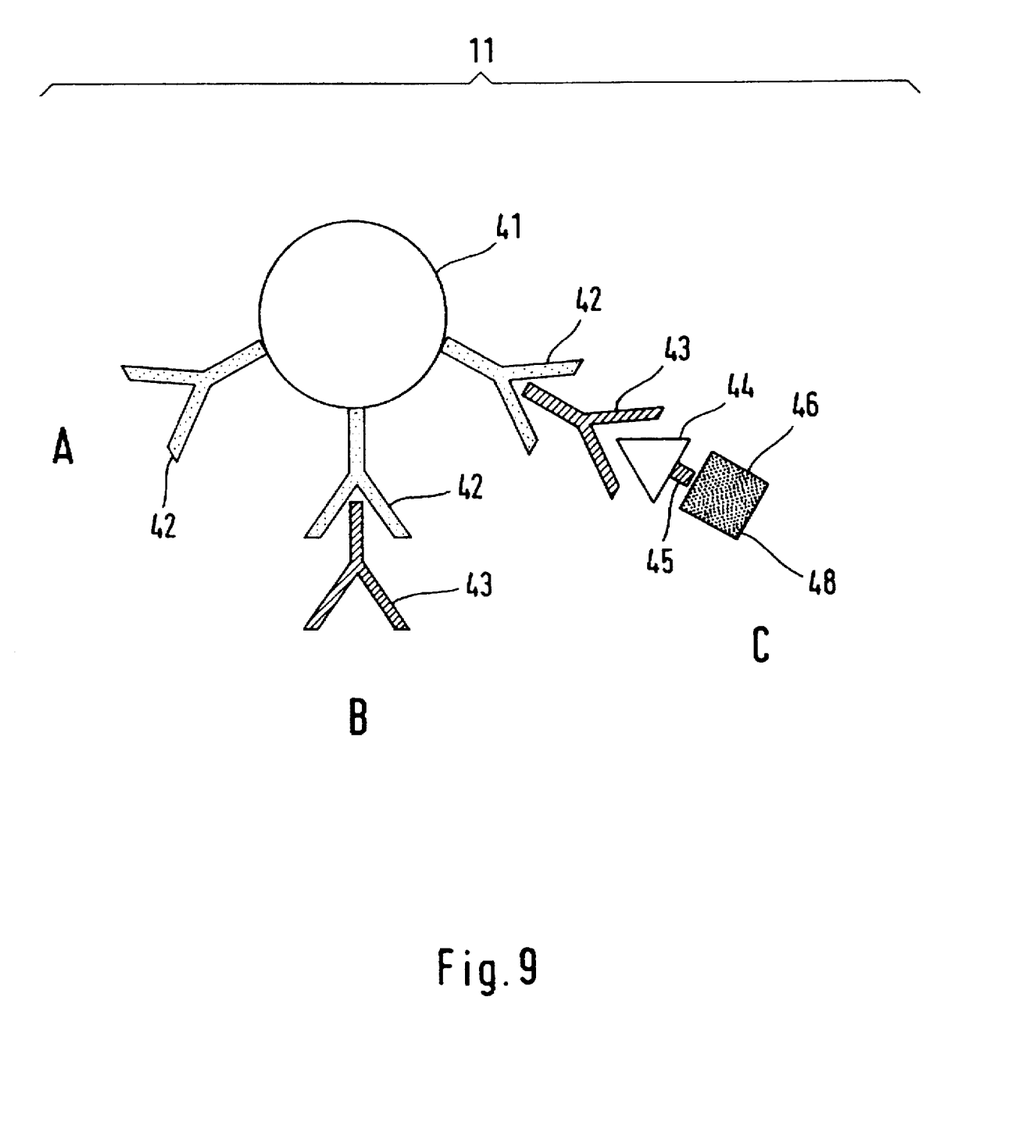
FIG. 9 is a schematic representation showing the structure of the immunological reaction component; and, FIG. 10 is a schematic representation of the reaction sequence for the immunological reaction component.

In the embodiments described, the immunochemical non-reactive component of the charge 11 in the reaction chamber 10 is shown on a pellet 41 as carrier (FIG. 9). Plastic pellets are known to workers in the area of immunoanalysis. These pellets, for example, of polystyrene, can be used as the so-called solid phase for the one-way reaction vessel according to the invention when they have suitable diameter for the reaction chamber 10. They are especially well suited when compared to glass powder or silica gel. The diameter or the configuration of the pellets 41 is so selected that air and liquid can always pass through the testing tube and that the pellets must not be orientated in a particular way when these pellets 41 are used in the reaction chamber. German Patent 3,448,006 discloses shapes of pellets which could be used in accordance with the invention. Accordingly, a coaxial arrangement of the pellets in the cylindrical testing tube according to the invention can be obtained when the pellets have radial projections. If the pellet has axial and end projections, then they can ensure that the pellet is held in spaced relationship to planar holding elements 15 and/or blocking layers 19 when testing tubes having a planar base are used. In this way, the free access of liquid to the largest possible contact surface of the charge 11 is maintained which reduces the immunoreaction time.

EXAMPLE 2

Manufacture of the Immunochemical Charge 11

The carrier 41 of the immunochemical charge 11 comprises polystyrene pellets as they are manufactured, for example, by Spherotech (Fulda, Germany) with a diameter of 4.76 mm. These pellets are coated in a first method step (FIG. 9, A) with anti-antibodies 42 which in this embodiment are anti-mouse immunoglobulines as available from DAKO (Hamburg, Germany) under the product designation Z 109. The first method step is performed as follows:

(a) 0.1 microliter of the anti-mouse antibody solution is applied to each pellet, that is, 0.12 microgram protein per pellet;

(b) 150 microliters of 0.05M PBS-buffer is additionally added for each pellet plus protein solution;

(c) pellets and protein buffer solution are incubated overnight at 37° C.; and, (d) thereafter, the supernatant is drawn off by suction or decanted and, thereafter, the pellets are washed three times with the purest water (that is, bidistilled $H_2O$).

In the second method step (FIG. 9B), the pellet is coated with the monoclonal or polyclonal antibody 43, which is specific to the aerosol to be analyzed, and, in this example, the pellets are coated with monoclonal anti-DNP antibody #51 as follows:

(a) 1 microliter of the anti-DNP antibody #51 solution is applied to each pellet, that is, 1 microgram protein per pellet;

(b) in addition, 150 microliters of 25 mNa-acetate buffer are applied to each pellet plus protein solution; and, (c) pellets and protein buffer solution are incubated for two hours at room temperature.

Binding sites which have possibly remained unoccupied are thereafter saturated with mouse serum (available from Sigma, Deisenhofen, Germany, as article number M5905) as delineated below:

(a) 1.5 microliters of mouse serum are applied to each pellet;

(b) pellets and mouse serum are incubated at room temperature for 1 hour;

(c) thereafter, the supernatant is drawn off by suction or decanted and, thereafter, the pellets are washed three times with the purest water (that is, bidistilled $H_2O$).

After this method step, the prepared, now immunochemically reactive pellets can be stored until further use, for example, in 0.05M PBS-buffer having 0.1% (w/v) Na-azide (Merck, Darmstadt, Germany, article number 882335) at 4° C. or, in the presence of stabilizers known per se to the person of skill in this field, in a dry state at room temperature.

In a third method step (FIG. 9, C), the specific antibody binding locations are saturated with tracer molecules 48 which are to be displaced during the actual aerosol measurement. The tracers 48 selected by way of example comprise dinitrophenol-lysine (DNP-L) 44, biotin 45 and streptavidin-beta-galactosidase 46.

The following steps are carried out to couple DNP-L with biotin:

(a) 3.2 mg NE-2,4-DNP-L-lysine hydrochloride (available from Sigma Company as article D-0380) and 4.5 mg biotinamidocaproat-N-hydrosysuccinimidester (available from Sigma Company as article B-2643) are dissolved in 500 microliters of water and amine-free DMF;

(b) 25 microliters pyridine (available from Aldrich, Steinhelm, Germany, as article 27,097-0, 99%) is added;

(c) the solution is incubated for at least 18 hours in the absence of light at room temperature;

(d) the reaction is stopped with 500 microliters of the purest water (that is, bidistilled $H_2O$);

(e) the reaction products and the constituents are separated by means of chromatography via tris-acryl GF05 column material (available from LKB, Uppsala, Sweden, as article no. 300-2500/810-2204), running buffer: 0.05M PBS-buffer, pH=8.0; and, (f) the chromatographic trace is followed by means of a photometer, the columnar eluate is trapped in a fractionated manner and thereafter, spectrophotometrically and immunochemically analyzed as known per se to the expert in the field.

The tris-acryl GF05 referred to above in paragraph (e) is a separating medium for molecular separation in accordance with the principle of size-exclusion chromatography. More specifically, as a solute passes down a chromatographic bed its movement depends upon the bulk flow of the mobil phase and upon the Brownian motion of the solute molecules which causes their diffusion both into and out of the stationary phase. The separation in gel filtration depends on the different abilities of the various sample molecules to enter pores, which contain the stationary phase. Tris-acryl GF05 is such a stationary phase for gel filtration. Molecules are eluted by gel filtration in order of decreasing molecular size.

The DNP-L-biotin-conjugate (44, 45) produced in the manner described above is now utilized as follows:

(a) 200 microliters of a 1:1,000 dilution of the immunochemically active composited chromatographic fractions are applied per pellet in 0.05M PBS-buffer and incubated at room temperature for one hour;

(b) the remaining DNP-L-biotin excess is thoroughly removed by washing with PBS-buffer;

(c) thereafter, the bonding between analyte derivative (DNP-L-biotin) and the streptavidin enzyme conjugate takes place (the biotinized analyte is bonded to the antibody);

(d) 200 microliters of a 1:1,000 dilution of the streptavidin-beta-galactosidase conjugate (available from Boehringer Mannheim, Mannhelm, Germany, as article no. 1112481, 500 U) are applied per pellet in 0.05M PBS-buffer and incubated for 0.5 hours at room temperature; and, (e) the remaining streptavidin-beta-galactosidase conjugate excess is thereafter thoroughly removed by washing with PBS-buffer.

The tracer 48 built up in this manner can now be displaced by the specific analyte 47 in the follow-on immunological displacement reaction from its binding to the antibody 43.

EXAMPLE 3

Immunochemical Reaction with Dinitrophenyl-Lysine as Analyte 47

The immunoreaction for detecting toxic aerosols takes place in accordance with the so-called "displacement principle" as described in the article of Kusterbeck et al entitled: "A continuous flow immunoassay for rapid and sensitive detection of small molecules", published in the Journal of Immunological Methods 135 (1990), pages 191 to 197. With this displacement immunoassay, a mixing of the samples with the tracer (the tracer can be analyte or analyte derivative upon which one or more marking elements are bonded) is unnecessary as it is required by competitive assays in order to start the competitive reaction for the limited antigen binding locations on the carrier. In such a displacement assay, separate reagent vessels or reagent layers including all reagents are unnecessary.

In the context of the invention, enzymes with the corresponding color substrates are the preferred tracers for the toxic substance aerosol detection.

In FIG. 10, the three essential reaction steps are schematically shown during the immunochemical reaction between analyte 47 and the participating reagents of the immunochemical charge 11 in the reaction chamber 10 of the testing tube according to the invention. The starting condition at the charge 11 during, for example, the storage of the reaction vessel and also during the aerosol collection and solution phase is shown in step D of FIG. 10. All available bonding sites of the specific antibodies 43 immobilized on the carrier 41 are saturated with an analyte derivative in the form of an enzyme-marked tracer 48. During the phase of bringing the solution from chamber 6 and/or collection layer 9 in contact with the charge 11 as well as during the subsequently defined incubation time, the tracer 48 is displaced by the analyte 47 (FIG. 10, E). For obtaining measurement values, those tracers are used which are provided with a marking and which are released during the immunochemical reaction proportional to the analyte concentration (FIG. 10, F).

In the example described here, the pellets produced pursuant to Example 2 are incubated with DNP-L-standards, that is, solutions of differently defined concentrations (obtainable from the Sigma Company as article no. D0380) as follows:

200 microliters of the DNP-L-standard solution are applied to each pellet and incubated at room temperature for 0.5 hour; and, thereafter, 150 microliters of the reaction solution are removed and incubated in an additional reaction vessel together with the enzyme substrate (see further below).

Applied to the embodiment of the one-way reaction vessel, this means that:

the solution is transferred to the granular reaction layer 49 of the enzyme reaction region 25 of the testing tubes. This reaction layer contains as enzyme substrate: chlorophenol red beta D galactopyranoside (CPRG, available from the Boehringer Mannheim Company as article no. 884308); after an incubation time of, for example, 15 minutes at room temperature, the reaction is stopped by adding 50 microliters of stop solution per pellet.

For the embodiment of the one-way reaction vessel as tube, this means the following:

after a defined reaction time, the more or less colored liquid is drawn by suction from the enzyme reaction layer 25 into the measuring chamber 12 by means of the gas pump. In the measuring chamber 12, enzyme inhibiting reagents 27 are located, for example, in lyophilized form which, after rehydration by the incoming liquid, stop the color-imparting reaction and thereby generate a measuring signal stabilized for a long term.

The evaluation of the measurement can be made by means of a color comparison with a color standard or, alternatively, spectrophotometrically at 574 or 578 nm.

In FIG. 9, the three phases (A, B and C) of the assembly of the immunochemical reactive charge 11 are shown schematically. As carrier or solid phase 41 for the immunoreaction, plastic pellets, for example, made of polystyrol, are used on which the preformed immuno complex for the subsequent immunochemical reaction is built up. The complex comprises a first immobilized specific anti-antibody-immunoglobulin 42 (FIG. 9, A), which binds selectively the anti-analyte-antibodies 43 (FIG. 9, B). Thereafter, analyte derivatives, for example, in the form of the enzyme-conjugate-tracers used here are selectively bonded to the anti-analyte-antibodies 43 (FIG. 9, C).

Figure 10:
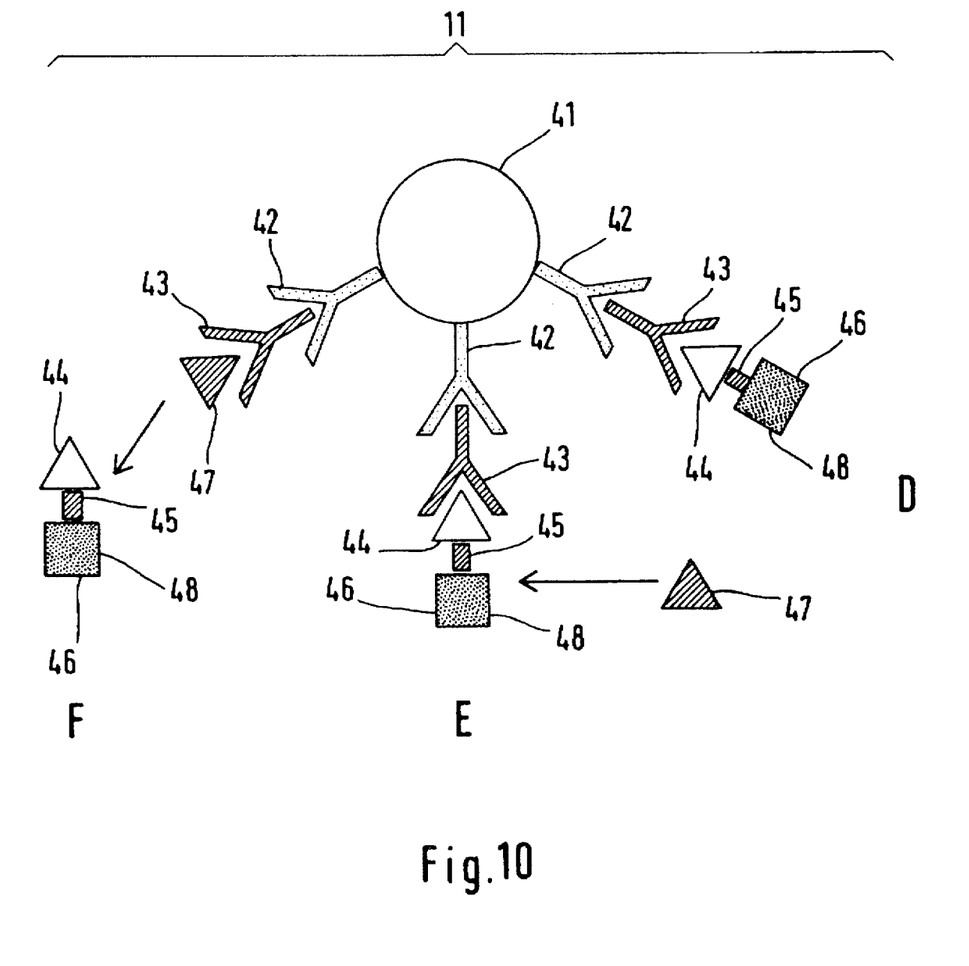

In FIG. 10, the three phases (D, E, F) of the invention are schematically shown during the immunochemical reaction. FIG. 10, D defines the starting state in which an analyte derivative (tracer 48) is bonded to the specific antibody 43. For the same specificity, but different affinity of analyte 47 and tracer 48 with respect to antibody binding, the tracer 48 is displaced by the analyte 47 from its antibody bond (FIG. 10, E) and released (FIG. 10, F). The released tracers 48 having a marking or color-imparting or color-generating system now permit a directly proportional measurement evaluation. The generated signal/marking is directly proportional to the analyte concentration in the specimen to be investigated.

Table: Buffers and Reagent Solutions (A) Enzyme substrate solution (CPRG solution): 3.29 mM CPRG in 100 mM HEPES (Biochrom, Berlin, Germany, article no. L1613); 150 mM NaCl (Sigma Company, article no. S9625); 10 mMMgCl (Merck Company, article no. 5832); 0.1% (w/v) Na-azide (Merck Company, article no. 882335); 1% (w/v) bovine serum albumin (Sigma Company, article no. A3294); pH=7.0.

B) stopper solution: 1M galactose (Sigma Company, article no. G0750); 0.1M EDTA (Merck Company, article no. 8418) in purest water (that is, bidistilled $H_2O$).

C) PBS-buffer (0.05M): dissolve 87 g di-potassium-hydrogen-phosphate (Merck Company, article no. 5104) and 17 g potassium-di-hydrogen-phosphate (Merck Company, article no. 4873) in 900 ml purest water (that is, bi-distilled $H_2O$), set pH value to 7.0 and fill up to 1,000 ml with purest water. Thereafter, dilute 1:10 in 0.9% (w/v) NaCl-solution (Clintec, Bad Homburg, Germany, article no. 45358).

D) Na-acetate-buffer (25 mM): dissolve 2.05 g sodiumacetate (Merck Company, article no. 6268) and 1.5 ml acetic acid (Merck Company, article no. 818755) in 1 liter purest water (that is, bidistilled $H_2O$); set pH value to 4.5.

It is understood that the foregoing description is that of the preferred embodiments of the invention and that various changes and modifications may be made thereto without departing from the spirit and scope of the invention as defined in the appended claims.

What is claimed is:

1. A reaction vessel for determining a toxic substance adhering to aerosols in an air sample, the reaction vessel comprising:

an elongated body having proximal and distal ends and enclosing a space defining at least a collection chamber, a reaction chamber and a measurement chamber in a sequential through-flow direction obtainable by attachment of a vacuum source to said distal end, wherein:

(a) said collection chamber contains at least a first breakable ampule filled with a liquid reagent for solubilizing and separating said toxic substance from said aerosols in order to transport said toxic substances into said reaction chamber;

a collecting layer comprising a semi-permeable means where said toxic substance adhered to said aerosols is deposited, arranged downstream from said first ampule, said semi-permeable means being permeable to said solubilized and separated toxic substance but impermeable to said aerosols; and, a first flow barrier disposed between said collecting layer and said reaction chamber for delaying liquid transport until said vacuum source is applied to pull said solublized and separated toxic substance therethrough into said reaction chamber;

(b) said reaction chamber contains an immunoreactive charge comprising a predetermined amount of a labelled reagent comprising a detectable label conjugated to said toxic substance or an analog thereof, said labelled reagent being complexed with (ii) a solid phase carrier material having immobilized thereon an immunoreactant which specifically binds to said toxic substance and said labelled reagent, such that any said solubilized and separated toxic substance entering said reaction chamber displaces said labelled reagent from said particles in proportion to the amount of said toxic substance present in said air sample; and, a second flow barrier disposed between said reaction chamber and said measurement chamber for delaying liquid transport from said reaction chamber for a defined reaction time until said vacuum source is applied to pull any displaced labelled reagent into said measurement chamber; and, (c) said measurement chamber contains a color generating system which reacts with said displaced labelled reagent to produce a colored product in proportion to the concentration of said toxic substance in said air sample.

2. The reaction vessel of claim 1, wherein said label is an enzyme and said color generating system comprises a chromogenic substrate which reacts with said enzyme to produce a colored product.

3. The reaction vessel of claim 2, wherein said enzyme substrate is in lyophilized form.

4. The reaction vessel of claim 2, wherein said measuring chamber further contains a second breakable ampule and said enzyme substrate is present as a solution in said second breakable ampule.

5. The reaction vessel of claim 2, wherein said measurement chamber sequentially comprises an enzyme reaction chamber containing said chromogenic substrate; signal measurement chamber; and, a third flow barrier disposed between said enzyme reaction chamber and said signal measurement chamber for delaying liquid transport from said enzyme reaction chamber into said signal measurement chamber for a defined reaction time until said vacuum source is applied.

6. The reaction vessel of claim 5, wherein said enzyme substrate is in dry form as a powder or a pill.

7. The reaction vessel of claim 5, wherein said enzyme reaction chamber holds a granular reaction layer; and, said enzyme substrate is in a dry form bonded to said granular reaction layer.

8. The reaction vessel of claim 5, further comprising an additional breakable ampule held in said enzyme reaction chamber; and, said enzyme substrate being a solution within said additional breakable ampule.

9. The reaction vessel of claim 5, wherein said signal measurement chamber contains a lyophilized an enzyme-inhibiting reagent for said enzyme label.

10. The reaction vessel of claim 5, wherein said signal measurement chamber contains a breakable ampule holding a liquid enzyme-inhibiting reagent for said enzyme label.

11. The reaction vessel of claim 1, wherein said immunoreactant is covalently or adsorptively bonded to said solid phase carrier material.

12. The reaction vessel of claim 1, wherein an antibody which specifically bonds to said immunoreactant is bonded to said solid phase carrier material; and, said immunoreactant is specifically bonded to said antibody.

13. The reaction vessel of claim 1, wherein said solid phase carrier material comprises plastic pellets.

14. The reaction vessel of claim 2, wherein said
enzyme label is conjugated to said toxic substance or said analog thereof either directly or indirectly through a linker comprising biotin.

15. The reaction vessel of claim 1, wherein said flow barriers are formed of hydrophobic material.

16. The reaction vessel of claim 15, wherein said hydrophobic material is a filter material.

17. The reaction vessel of claim 1, wherein said semi-permeable means is formed of an inert membrane having a defined pore diameter.

18. The reaction vessel of claim 1, wherein said semi-permeable means is formed of a quartz glass fabric.

19. The reaction vessel of claim 1, wherein said collecting layer further comprises a layer of granular quartz between said semi-permeable means and said first flow barrier.

20. The reaction vessel of claim 5, wherein said signal measurement chamber further comprises an enzyme-inhibiting reagent for said enzyme label for stopping production of said colored product.

* * * * *

UNITED STATES PATENT AND TRADEMARK OFFICE
CERTIFICATE OF CORRECTION

PATENT NO. : 5,633,140             page 1 of 2

DATED : May 27, 1997

INVENTOR(S) : Kerstin Wex, Thomas Wuske and Andreas Manns

It is certified that error appears in the above-identified patent and that said Letters Patent is hereby corrected as shown below:

In column 5, line 61: delete "brake" and substitute -- break -- therefor.

In column 7, line 32: delete "ampnle" and substitute -- ampule -- therefor.

In column 9, lines 38 and 39: "spectrophotometrically and immunochemically analyzed as known per se to the expert in the field." should be indented as part of paragraph "(f)".

In column 11, line 7: after "vessel as" insert -- a -- .

In column 11, line 50: delete "10mMMgCl(Merck" to read --10mMMgCl$_2$ (Merck--.

UNITED STATES PATENT AND TRADEMARK OFFICE
CERTIFICATE OF CORRECTION

PATENT NO. : 5,633,140

DATED : May 27, 1997

INVENTOR(S) : Kerstin Wex, Thomas Wuske and Andreas Manns

It is certified that error appears in the above-identified patent and that said Letters Patent is hereby corrected as shown below:

In column 12, line 34: delete "solublized" and substitute -- solubilized -- therefor.

In column 12, line 38: before "a predetermined" insert -- (i) --.

In column 13, line 7: between "substrate;" and "signal" insert -- a --.

In column 13, line 25: between "lyophilized" and "enzyme-" delete "an".

Signed and Sealed this

Seventh Day of October, 1997

Attest:

BRUCE LEHMAN

*Attesting Officer*  *Commissioner of Patents and Trademarks*